(12) United States Patent
Lim et al.

(10) Patent No.: US 9,358,078 B2
(45) Date of Patent: Jun. 7, 2016

(54) IMAGING DEVICE AND METHOD

(71) Applicant: NATIONAL UNIVERSITY OF SINGAPORE, Singapore (SG)

(72) Inventors: Beng Hai Lim, Singapore (SG); Timothy Poston, Bangalore (IN); James Kolenchery Rappel, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 33 days.

(21) Appl. No.: 14/140,907

(22) Filed: Dec. 26, 2013

(65) Prior Publication Data

US 2014/0285632 A1  Sep. 25, 2014

Related U.S. Application Data

(63) Continuation of application No. 12/526,886, filed as application No. PCT/SG2008/000053 on Feb. 13, 2008, now abandoned.

(60) Provisional application No. 60/889,674, filed on Feb. 13, 2007.

(51) Int. Cl.
*G02B 21/22* (2006.01)
*G02B 21/00* (2006.01)
*A61B 19/00* (2006.01)
*A61B 1/00* (2006.01)
*G02B 27/22* (2006.01)
*H04N 13/02* (2006.01)
*H04N 13/04* (2006.01)

(52) U.S. Cl.
CPC .............. *A61B 19/5225* (2013.01); *A61B 19/26* (2013.01); *A61B 19/52* (2013.01); *A61B 19/5223* (2013.01); *G02B 27/2264* (2013.01); *H04N 13/0239* (2013.01); *H04N 13/0429* (2013.01); *A61B 19/5212* (2013.01); *A61B 2019/262* (2013.01); *A61B 2019/5227* (2013.01); *A61B 2019/5229* (2013.01); *A61B 2019/5295* (2013.01)

(58) Field of Classification Search
None
See application file for complete search history.

(56) References Cited

U.S. PATENT DOCUMENTS 5,535,060 A * 7/1996 Grinblat ........................ 359/835
5,749,362 A * 5/1998 Funda et al. .................. 600/407
(Continued)

FOREIGN PATENT DOCUMENTS

EP  1621153 A1  2/2006
JP  2002-287033 A  10/2002
(Continued)

OTHER PUBLICATIONS

European Patent Office, Extended European Search Report for Application No. 08712878.1, Jul. 27, 2011, 6 pages, Netherlands.
(Continued)

*Primary Examiner* — Nicholas Taylor
*Assistant Examiner* — Ho Shiu
(74) *Attorney, Agent, or Firm* — Alston & Bird LLP

(57) ABSTRACT

An imaging system comprising an image capture apparatus, arranged to capture a stereoscopic image of an operator work site, in communication with a display system; the display system arranged to receive and display said stereoscopic image on a display screen to said operator; wherein said display system is arranged such that the display screen is placed intermediate the operator's eyes and the work site.

10 Claims, 4 Drawing Sheets

(56) References Cited

U.S. PATENT DOCUMENTS

| | | | | |
|---|---|---|---|---|
| 5,865,829 | A * | 2/1999 | Kitajima | 606/3 |
| 6,396,627 | B1 * | 5/2002 | Tachihara et al. | 359/363 |
| 6,429,418 | B1 * | 8/2002 | Chahl et al. | 250/216 |
| 6,522,310 | B1 * | 2/2003 | Kim | 345/6 |
| 6,525,878 | B1 * | 2/2003 | Takahashi | G02B 21/0012 |
| | | | | 359/376 |
| 6,926,409 | B2 | 8/2005 | Togino et al. | |
| 6,927,905 | B1 * | 8/2005 | Kashitani et al. | 359/402 |
| 7,180,663 | B2 * | 2/2007 | Collender et al. | 359/451 |
| 2001/0031081 | A1 * | 10/2001 | Quan et al. | 382/154 |
| 2002/0067411 | A1 * | 6/2002 | Thompson et al. | 348/207 |
| 2002/0082466 | A1 * | 6/2002 | Han | A61B 18/20 |
| | | | | 600/13 |
| 2003/0063293 | A1 * | 4/2003 | Kitabayashi | G01M 11/00 |
| | | | | 356/614 |
| 2003/0069471 | A1 * | 4/2003 | Nakanishi et al. | 600/101 |
| 2003/0071893 | A1 * | 4/2003 | Miller et al. | 348/42 |
| 2003/0142203 | A1 * | 7/2003 | Kawakami et al. | 348/36 |
| 2003/0174292 | A1 * | 9/2003 | White | 353/74 |
| 2004/0049111 | A1 * | 3/2004 | Hirooka et al. | 600/437 |
| 2004/0085517 | A1 * | 5/2004 | Togino et al. | 353/31 |
| 2004/0125447 | A1 * | 7/2004 | Sato et al. | 359/462 |
| 2004/0155956 | A1 * | 8/2004 | Libbey | 348/14.16 |
| 2004/0196438 | A1 * | 10/2004 | Togino | 353/30 |
| 2004/0220464 | A1 * | 11/2004 | Benninger et al. | 600/407 |
| 2005/0020876 | A1 * | 1/2005 | Shioda et al. | 600/101 |
| 2005/0030489 | A1 * | 2/2005 | Togino | 353/74 |
| 2005/0047172 | A1 * | 3/2005 | Sander | 362/554 |
| 2005/0117118 | A1 * | 6/2005 | Miller et al. | 351/246 |
| 2005/0180019 | A1 * | 8/2005 | Cho et al. | 359/626 |
| 2005/0248972 | A1 * | 11/2005 | Kondo et al. | 365/125 |
| 2005/0285038 | A1 * | 12/2005 | Frangioni | A61B 5/0059 |
| | | | | 250/330 |
| 2006/0004292 | A1 * | 1/2006 | Beylin | 600/476 |
| 2006/0135866 | A1 * | 6/2006 | Namii et al. | 600/407 |
| 2006/0142897 | A1 * | 6/2006 | Green | 700/245 |
| 2006/0166737 | A1 * | 7/2006 | Bentley | 463/30 |
| 2006/0181607 | A1 * | 8/2006 | McNelley et al. | 348/14.08 |
| 2007/0035493 | A1 * | 2/2007 | Chang | 345/87 |
| 2007/0058035 | A9 * | 3/2007 | Fujie et al. | 348/66 |
| 2007/0127115 | A1 * | 6/2007 | Hauger et al. | 359/376 |
| 2008/0142597 | A1 * | 6/2008 | Joseph et al. | 235/462.21 |

FOREIGN PATENT DOCUMENTS

| | | |
|---|---|---|
| JP | 2004-177920 A | 6/2004 |
| WO | WO 95/14252 A1 | 5/1995 |
| WO | WO 2005/109068 A1 | 11/2005 |

OTHER PUBLICATIONS

Japan Patent Office, Office Action for Application No. 2009-550089, Sep. 25, 2012, 6 pages, Japan.
United States Patent and Trademark Office, Office Action for U.S. Appl. No. 12/526,886, Apr. 9, 2012, USA.
United States Patent and Trademark Office, Office Action for U.S. Appl. No. 12/526,886, Dec. 20, 2012, USA.
United States Patent and Trademark Office, Office Action for U.S. Appl. No. 12/526,886, Jun. 25, 2013, USA.

* cited by examiner

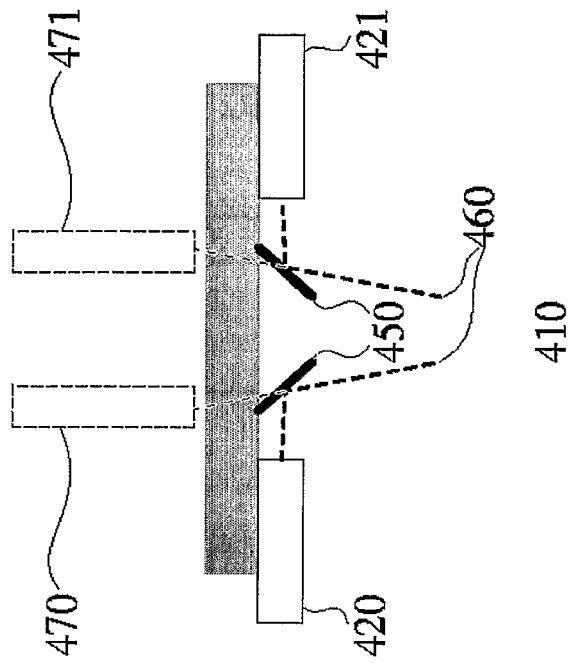
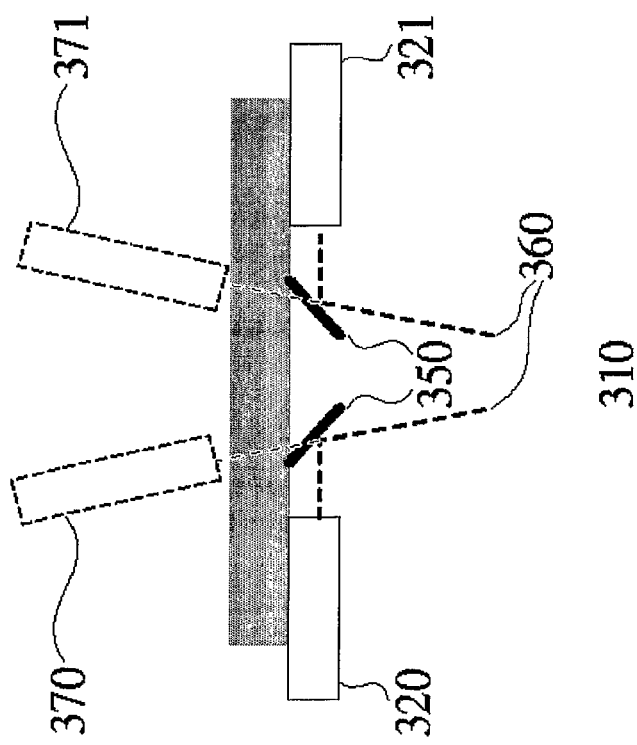

IMAGING DEVICE AND METHOD

CROSS REFERENCE TO RELATED APPLICATIONS

This application is a continuation of U.S. application Ser. No. 12/526,886, filed Dec. 22, 2009, which was a national stage application, filed under 35 U.S.C. §371, of International Application No. PCT/SG08/00053, filed Feb. 13, 2008, which claims benefit of U.S. Provisional Application No. 60/889,674, filed Feb. 13, 2007, the contents all of which are hereby incorporated by reference in their entirety.

FIELD OF THE INVENTION

The present invention relates to the fields of stereo microscopy and digital stereo display.

BACKGROUND OF THE ART

Modern reconstructive surgery was made possible by the stereo microscope. Early work showed that skin cannot simply be grafted—cut from one place and reattached in another—without attention to its blood supply. With no artery feeding it, it dies. Maintaining the old blood vessels while new ones grow from the attachment site places narrow constraints, on what donor and target sites can be combined.

This problem is solved by the transplant of more than skin: a surgical flap includes underlying tissue, and blood vessels which the surgeon joins to vessels in the target site. Since the vessels involved may be less than 1 mm in diameter, the accurate placement of six small sutures for a join where the blood flow without leaking requires magnification. This means more than merely an enlarged view. Dexterity in suturing requires depth perception, so that the needle can penetrate at a correct angle, including angles away from the viewer. The depth cue of parallax is unavailable through a microscope with a fixed viewpoint, perspective is unhelpful in a view with no straight lines and limited focal depth, and occlusion cannot show how far above the needle is above the tissue. It is essential to have the depth cue of stereopsis, with a lens system for each eye delivering views from different angles, to the two eyepieces. We refer to a pair of views that permit stereopsis as a stereo view or stereoscopic view, or as one having stereo. If the difference is correctly structured, the user's brain integrates the two views into a single scene with perceived depth, just as for direct vision with two eyes. Much surgery depends critically on this, as does dexterous work in other domains, such as industrial micro-assembly.

However, the surgical microscope requires that the user's head remain perfectly fixed, keeping the eyes to the eyepieces, throughout a long series of delicate procedures with substantial risk. This is an important source of stress on the surgeon, causing pain in the neck and back, and requiring several rest pauses per hour.

An alternative to enlarged display through optical lenses is to show on an electronic display the output of a real-time camera, digital or analogue. This technology is available, but in forms that fail to support stereo, that require the user to look away from the hands at a rotated view, or have both these problems. A view rotated from the natural direction requires the user to handle the fact that "to turn the instrument in the image this way, I must turn my hands that way," adding to the cognitive difficulty, strain and learning curve of the task.

STATEMENT OF INVENTION

Therefore, in a first aspect, the invention provides an imaging system comprising an image capture apparatus, arranged to capture a stereoscopic image of an operator work site, in communication with a display system; the display system arranged to receive and display said stereoscopic image on a display screen to said operator; wherein said display system is arranged such that the display screen is placed intermediate the operator's eyes and the work site.

In a second aspect, the invention provides a method for displaying an image, comprising the steps of: capturing a stereoscopic image of an operator work site; communicating said image to a display system; displaying said stereoscopic image on a display screen placed intermediate the operator's eyes and the work site.

A panel is placed over the work site, at a height sufficient to allow the insertion of instruments or tools. On this panel may be placed a fast display (LCD or OLED, or other such technologies as they arise, and which will be clear, to the skilled person) alternating between enlarged views of left and right camera images from below the panel. The two distinct images may come from two cameras, or alternatively by suitable mirror arrangements from a single camera. Depending on the optical layout, the camera or cameras may be entirely under the panel, or partially protrude from under it.

The operators or operators (as in the case of two surgeons cooperating in a single procedure) may wear shutter glasses which block out alternate views, leaving visible the view appropriate to each eye. This creates an enlarged view of the work site, appearing to the visual system of the user in substantially the same location and orientation as they appear to the user's motor cortex, via the neuromotor system of the user's arm and hands. Motions of an operator's head may make small differences in the visually apparent placement in 3-dimensional space of the objects in the work site, natural or inserted, but may still permit effective coordination of manual control of tools and instruments with what is apparent to the visual system.

BRIEF DESCRIPTION OF DRAWINGS

FIGS. 3 and 4 show alternative configurations of the two-camera setup of FIG. 2;

It will be convenient to further describe the present invention with respect to the accompanying drawings that illustrate possible arrangements of the invention. Other arrangements of the invention are possible, and consequently the particularity of the accompanying drawings is not to be understood as superseding the generality of the preceding description of the invention.

DESCRIPTION OF PREFERRED EMBODIMENT

Figure 1:
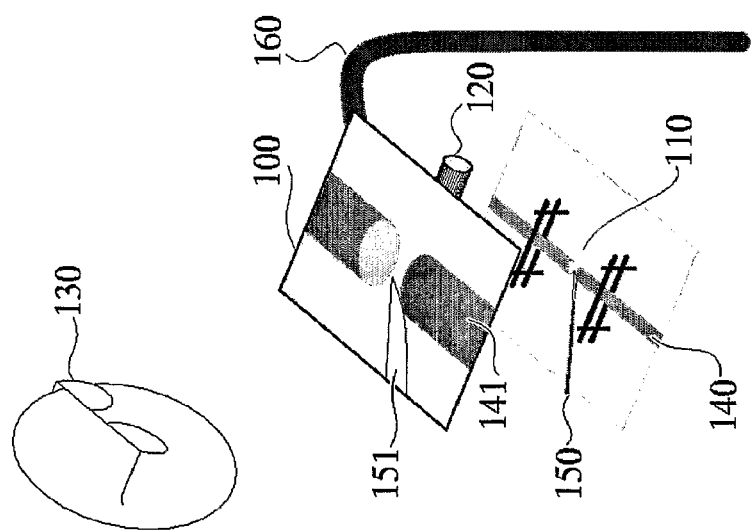
FIG. 1 is a perspective view of an embodiment of an imaging system.
Figure 6:
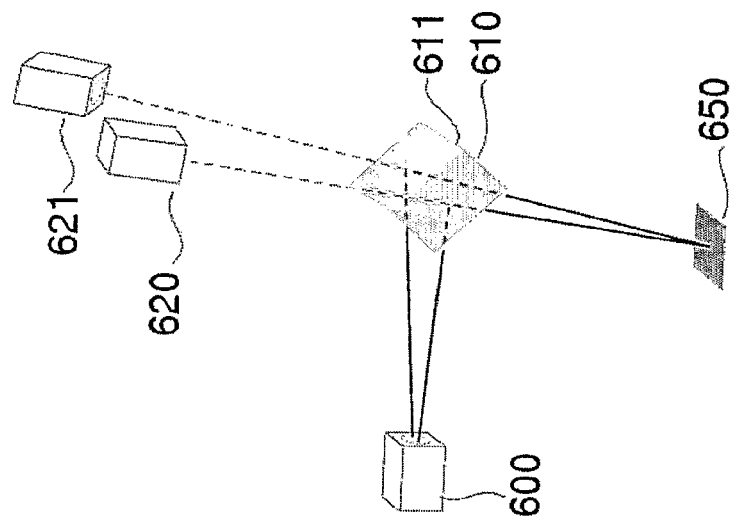
FIG. 6 shows an alternative configuration of the single-camera setup of FIG. 5.

FIG. 1 shows a display panel 100 over a work site 110, using a rigid support 160. The display panel 100 may be an LCD panel, and in this case is supported by a flexible arm 160. The arm is sufficiently strong to support the panel 100, and also flexible enough to be moved so as to position the panel for the convenience of the operator.

In this case, the work site 110 involves micro-surgery, whereby an artery 140 is undergoing re-attachment. The artery 140 and scalpel 150 are illustrative of the items present on a work site 110, appearing enlarged as arteries 141 and scalpel tip 151 on the display panel 100, by an enlargement factor adjustable from 2 to a number on the order of 20. (Human fine motor control limits the useful degree of enlargement. For most practitioners, magnification above 15-fold may display tremor.) The height of the panel 100 above the work site 110 may be adjustable or fixed in a particular implementation, but may vary between 2 cm for high enlargement to 20 cm for smaller magnification factors. Particular implementations may vary the panel size for applications that use particular ranges of magnification, but our initial preferred embodiment uses a panel approximately 15 cm×15 cm square at a height of approximately 8 cm above the work site.

In the preferred embodiment shown in FIG. 1, the stereoscopic effect is achieved by alternating left and right views with synchronized shutter glasses 130, worn by the operator/surgeon to control which eye sees which view, but a glasses-free 'autostereo' solution may also be used if it has sufficient resolution and supports stereo over a wide enough range of head motion for user comfort. Similarly, if real-time holographic cameras and enlarged holographic views become practical, they may be used within the ambit of the present invention.

Figure 2:
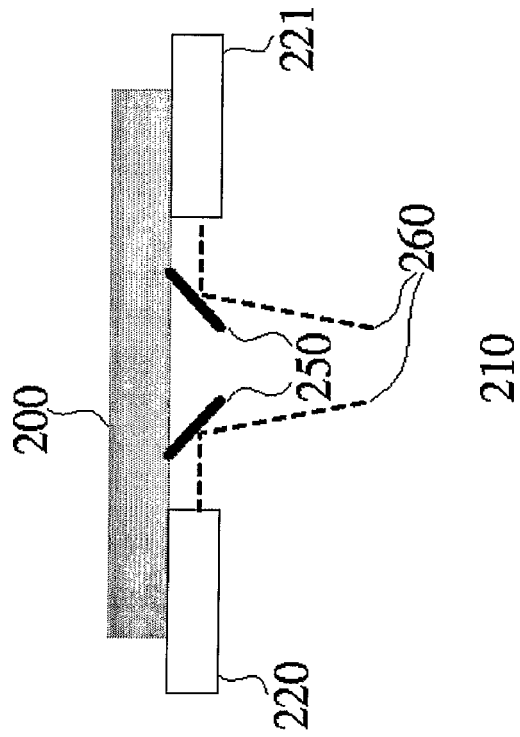
FIG. 2 is a plan view of an exemplary two-camera setup for an imaging system according to embodiments.

The views shown on the display 100 are taken by one or two cameras 120. An exemplary two-camera configuration is shown in FIG. 2. A left-eye camera 220 and a right-eye camera 221 lie under the display panel 200, pointing at mirrors 250. Light from the work site 210 travels, via the mirrors 250, to the cameras 220 and 221 which create images to be shown on the display panel 200. The dashed lines 260 show paths along which light is reflected to cameras 220 and 221. The placement of the mirrors creates the disparity of angle between the two views, geometrically analogous to the difference between the viewing directions between two unassisted human eyes, which creates the stereoptic perception of depth when the views are shown on the display 200 and channeled to the appropriate eyes by the shutter glasses 130, or other stereo display mechanism used in the chosen embodiment. Typically an angle of approximately 6° between the lines 260, matching the angular disparity of views of an object a half-meter distant from eyes at a representative 6 cm separation in the human face, will give a satisfactory experience of depth perception to the user, with an apparent visual position for the center of the work site 210 that is substantially in agreement with the position at which the user experiences it via the hands. (There cannot be exact agreement in position between the physical objects and their stereo images, matching them point by point, since the images are arranged to be larger.) Optionally, the positions and angles of the mirrors 250 may be made user-adjustable, to customize the viewing experience to the preferred head distance and to human variation in eye separation.

The apparent depth may also be modified in software, by moving the left and right images in opposite sideways senses across the display, in ways familiar to those skilled in the art.

In our initial preferred embodiment the mirrors 250 are planar, serving only the function of redirecting the view of cameras 220 and 221, but optionally they may be curved, contributing to the focusing geometry by which the images are created. In the case where the mirrors 250 are planar, the images collected by the cameras, as shown in FIG. 3, are precisely those that would be collected by cameras in the locations 370 and 371, unobstructed by the mirrors 350 or the display panel 300. The cameras 320 and 321 thus correspond to 'virtual cameras' in these positions 370 and 371. It should be noted that if the real cameras are horizontal (for most efficient use of space) and the light paths 260 correspond to the central point of each image (centering the same work site point in the image), the virtual cameras are not parallel in their viewing axes. Such parallelism is required for optimal stereoscopic viewing: the eyeballs rotate to nonparallel angles in viewing a stereoscopic display, but unless each eye has a separate screen which moves to remain at right angles to the eye's central line of sight, this does not mean that the camera angles should rotate. Where there is a display screen shared between the left and right views, each camera axis should be at right angles to that screen. This is possible for the virtual cameras 470 and 471, by the use of 45° mirror angles 450 as shown in FIG. 4. (The light paths 460 to the center of the work site 410 are not in this case central to the field of view of the cameras 420 and 421.) Alternatively, a projective transformation in software can adjust the camera views to those that would be acquired by parallel-axis cameras. In every embodiment that uses mirrors, software must transform the camera image to compensate for the optical view reversal by the mirror, so that the direction of any motion in the displayed image agrees substantially with the direction of the real-world motion to which it corresponds.

Figure 5:
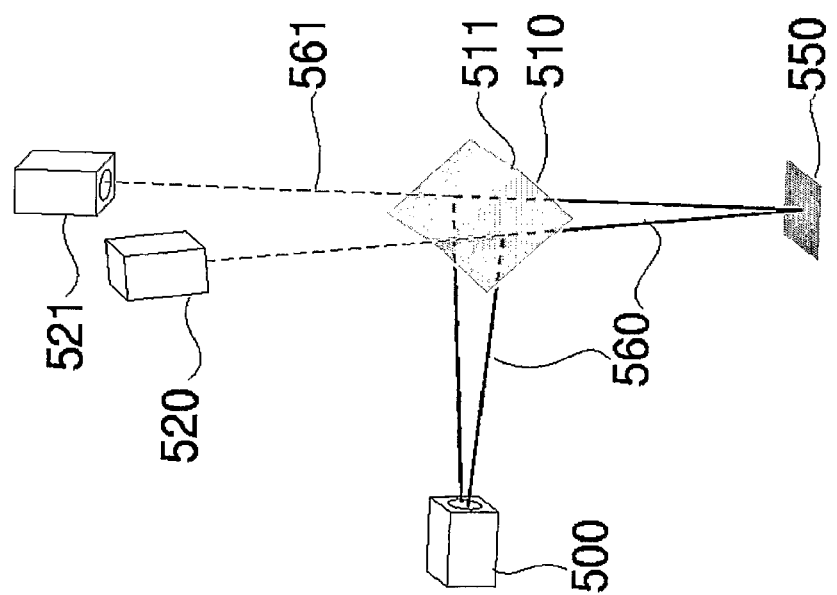
FIG. 5 is a perspective view of a single-camera setup for an imaging system.
Figures 7, 8:
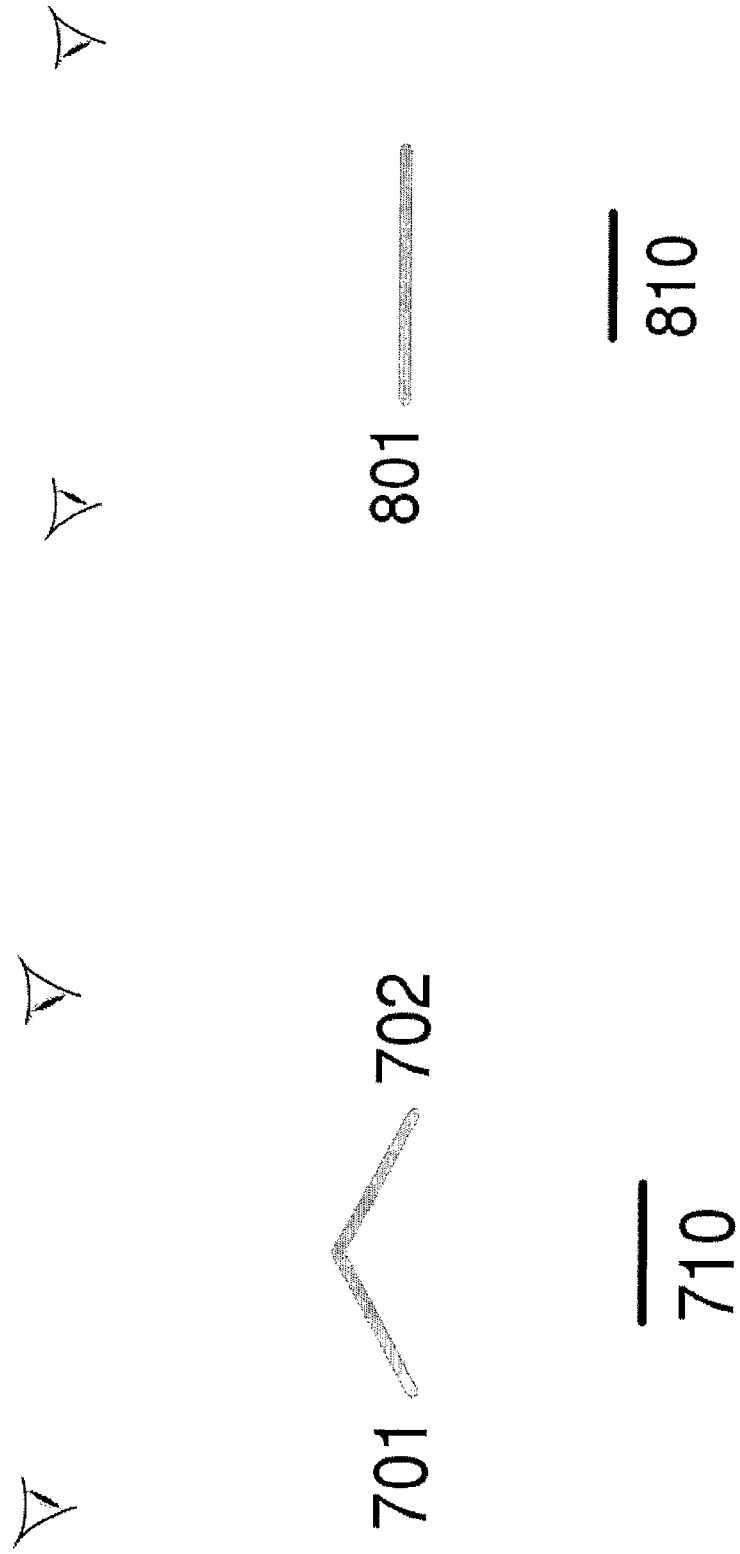
FIG. 7 is a schematic illustration of a system with two displays in use by two surgeons.
FIG. 8 is a schematic illustration of a system with a single display in use by two surgeons.

As an alternative to the two-camera system shown in FIGS. 2, 3 and 4, a single camera may be used. FIG. 5 shows a configuration to be placed under the display panel 100, with a horizontal camera 500 directed at a mirror directly over the work site 550. The mirror has two planar sections 510 and 511, which are close to the 45° angle previously shown but angled slightly inward. The exact choice of mirror angle depends on the desired placement of the virtual cameras 520 and 521, which 'see' along the virtual rays 561 what the real camera sees along the reflected real rays 560: the angle may be found by computations (involving also the chosen distances from camera 500 to the mirror sections 510 and 511, and the distance above the work site to be imaged by both views) which are straightforward to one skilled in the art. This configuration necessarily requires a software adjustment to create the images that would be acquired by parallel cameras, as well as software reversal of the mirror reversal.

It is not essential that the display panel 100 be horizontal. While this is most convenient where (as in certain surgical procedures) a single stereoscopic view is to be shared between two collaborating users, a more comfortable view may in some circumstances be obtained by tilting the display panel toward the viewer, who can then look orthogonally at it from a less forward posture. The precise tilt appropriate is a choice that depends on ergonomic factors such as preferred posture for sustained micro-dexterous work, and requires careful study for each application. It will in some cases be preferable to make the angle adjustable, so that users can adapt it to their own comfort and convenience according to habit and body type.

Specifically for collaboration and training, an alternative model would include two display panels tilted like the sides of a roof and meeting along the ridge line, each showing the same stereoscopic view from the same camera or pair of cameras. This is preferred to giving each panel a distinct stereoscopic view, both for reasons of economy and to ensure that each user sees exactly the same view (though slightly differently distorted by individual departures from the reference eye positions for which the system is optimized). Such an identity of stereoscopic view minimizes the risk of miscommunication between surgeons, or between instructor and trainee, as to what a particular utterance refers to: for example, if a scalpel tip is used as a pointer, the same physical point will appear exactly behind it in both views.

As described so far, the views correspond to magnified versions of those seen by a pair of eyes set in a face looking vertically downward. As FIG. 1 illustrates, however, the surgeon's eyes are typically not directly above the surgical site. Exactly vertical views would thus create a certain degree of mismatch: for example, an object moved vertically in the physical scene would seem in the virtual scene to rise straight toward the viewer, in disagreement with the user's sense of direction in the control of his or her hands. For a single viewer this may be corrected by simply tilting the display screen, replacing the vertical direction by the straight line from the work site to bridge of the surgeon's eyes.

Alternatively, however, we may slightly tilt the mirror pair 510 and 511 (or similarly for a two-camera configuration). If we do this so that their common line is closer than 45° to the vertical, the plane of the virtual cameras 620 and 621 and the work site 650 tilts through twice this change, and we produce a view appropriate for a surgeon facing the apparatus from the side opposite to the camera. Tilting in the opposite direction gives a view appropriate to a surgeon on the side near the camera. (There is also a necessary adjustment in the height of the image shown on the display 100, allowing for the foreshortening in the surgeon's view of the said display, easily accomplished by software manipulation of the image.)

Many microsurgical procedures involve two cooperating surgeons, on opposite sides of the surgical site. The tilt just described cannot be adjusted correctly for both of them in the same image. The most economical solution is to accept the vertical view as a compromise that they both see, as in the two-user surgical microscope currently in use for this purpose. Alternatively, they can each have their own tilted display 701 and 702 for viewing the work site 710 in their natural directions, or they can share a single display 801 in which four images alternate: the views for Surgeon 1 left eye, Surgeon 2 left eye, Surgeon 1 right eye and Surgeon 2 right eye, showing appropriate views of the work site 810, acquired by one, two or four cameras according to the mirror arrangement used: appropriate mirror configurations generalizing those in Drawings 2 to 6 will be evident to one skilled in the art. This requires a display that is capable of cycling between four images in the 1/60 sec. that is a comfortable standard for moving video, and shutter glasses synchronised with it that can prevent each eye from seeing the three images that are not intended for it, out of each sequence of four. The required frame rate of 240 per second seems unlikely for LCD technology at this time, but is well within the potential capability of OLED displays.

The invention claimed is:

1. An imaging system for capturing a stereoscopic image of a surgery work site and displaying the stereoscopic image to a surgery operator, the imaging system comprising:

an image capture apparatus, arranged to capture a stereoscopic image of a microsurgical work site, in communication with a display system;

the display system arranged to receive and display said stereoscopic image on a display screen to said operator;

wherein the display screen is supported by a selectively movable frame so as to be capable of selectively moving the display screen into and out of alignment of the operator's eyes and the microsurgical work site;

wherein said image capture apparatus includes a pair of cameras, the difference in images captured by said cameras consistent with the difference in images captured by the unassisted eyes of the operator;

wherein said image capture apparatus further includes mirrors corresponding to each camera, the mirrors being arranged to direct the respective images to said corresponding cameras along paths substantially parallel to the display screen and so display the stereoscopic image at an angle the same as that of the operator's unassisted eyes so as to provide stereoscopic depth perception for the spatial relationship of elements with the microsurgical work site.

2. The system according to claim 1, wherein said movable frame comprises a resiliently deformable arm mounted between said frame and an anchor point, said arm capable of deforming to a range of positions subject to the requirements of the operator.

3. The system according to claim 1, further including shutter glasses, wearable by the operator to provide alternating images shown on the display screen to the operator.

4. The system according to claim 1, wherein the display screen displays the images directed in differing directions so as to permit each image to correspond with the relevant eye.

5. The system according to claim 1, wherein said mirrors are curved.

6. The system according to claim 1, wherein the display system includes two display screens so as to permit two operators working simultaneously within the work site to view the stereoscopic image.

7. The system according to claim 1, wherein the display screen alternates four images corresponding to two pairs of images so as to permit two operators working simultaneously within the work site to view the stereoscopic image.

8. The system according to claim 1, wherein said cameras and said mirrors are located below said display screen and between said display screen and the work site.

9. The system according to claim 1, wherein said stereoscopic image of the work site is displayed on said display screen at substantially the same location and orientation as would be seen of the work site with the unassisted eyes of the operator.

10. The system according to claim 8, wherein said cameras each have an axis aligned horizontally with respect to the display screen.

* * * * *